United States Patent
Bourassa (10) Patent No.: US 6,358,217 B1
(45) Date of Patent: Mar. 19, 2002

(54) AUTOMATIC AND SEMI-AUTOMATIC DISPOSABLE BIOPSY NEEDLE DEVICE

(76) Inventor: Hugh Bourassa, 32212 Corte Gabaiva, Temecula, CA (US) 92592

( * ) Notice: Subject to any disclaimer, the term of this patent is extended or adjusted under 35 U.S.C. 154(b) by 0 days.

(21) Appl. No.: 09/494,895

(22) Filed: Jan. 31, 2000

(51) Int. Cl.$^7$ ................................................. A61B 5/00
(52) U.S. Cl. .................................................... 600/567
(58) Field of Search ........................ 600/562, 564–567; 606/167, 170, 172

(56) References Cited

U.S. PATENT DOCUMENTS

| | | | |
|---|---|---|---|
| 4,881,551 A | 11/1989 | Taylor | 128/754 |
| 4,907,599 A | 3/1990 | Taylor | 128/754 |
| 4,924,878 A | 5/1990 | Nottke | 128/751 |
| 4,953,558 A | 9/1990 | Akerfeldt | 128/751 |
| 4,958,625 A | 9/1990 | Bates et al. | 128/754 |
| 5,172,702 A | 12/1992 | Leigh et al. | 128/754 |
| 5,335,672 A | 8/1994 | Bennett | 128/754 |
| 5,505,211 A | 4/1996 | Ohto et al. | 128/754 |
| 5,507,298 A | 4/1996 | Schramm et al. | 128/754 |
| 5,718,237 A | 2/1998 | Haaga | 128/751 |

Primary Examiner—Max Hindenburg
(74) Attorney, Agent, or Firm—Eric Karich (57) ABSTRACT

The biopsy needle device has an axially elongated stylet and a cannula coaxially disposed thereabout, the stylet and cannula being mounted on stylet and cannula bases that are slidably mounted within a cavity of an elongate housing. The cavity also contains a spring-loaded firing mechanism for firing the stylet and cannula for taking a tissue sample from a patient. The stylet base contains a safety stylet latch lever and a firing stylet latch lever for retaining the stylet in the first, retracted position until released. The cannula base includes a safety cannula latch lever and a locking cylinder for retaining the cannula base in the first retracted position until released. Once the safety and firing stylet latch levers have been released, the stylet base advances to contact a finger of the stop pad, thereby releasing the safety cannula latch lever. The tissue of the patient prolapses into a side-facing notch of the advancing stylet. Once the locking cylinder has been released with a cannula firing button, the cannula base advances to contact the stop pad, thereby causing the cannula to advance to cover the side-facing notch, thereby severing and containing the tissue. In the preferred embodiment, the stop pad is threaded engaged upon an adjustment screw; and the stop pad transmits the force of the impact of both the stylet and cannula bases through the adjustment screw to a resilient diaphragm of the housing, thereby dampening the force of the impacts.

8 Claims, 7 Drawing Sheets

AUTOMATIC AND SEMI-AUTOMATIC DISPOSABLE BIOPSY NEEDLE DEVICE

BACKGROUND OF THE INVENTION

1. Field of the Invention

This invention relates generally to biopsy needle devices, and more particularly to a disposable biopsy needle device that includes a safety latch and can be used in either an automatic or semi-automatic firing mode, the biopsy needle device having a dampening system that operates to minimize recoil when the device is fired.

2. Description of Related Art

Various biopsy needle devices are known in the art. A typical biopsy needle device known in the art uses a "stylet" in conjunction with a "cannula," both described more fully, to cut a small tissue sample from a precise location within a patient. The stylet and cannula then function to remove the sample from the body for analysis. The typical biopsy needle device of the type comprising (a) an elongate housing, (b) a knob 104 at the first end of the housing, (c) first and second pistons extending from the second end of the housing, (d) connections on the extending ends of the pistons for connecting the stylet and cannula respectively, (e) first and second springs in the housing against which the first and second pistons, respectively, are cocked so that the springs apply a biasing force against the respective pistons, (f) a trigger successive movements wherein the first piston moves force of the first spring while the second piston remains in its cocked position, and after the first piston has moved to its fully extended position, the second piston moves to its fully extended position under the biasing force of the second spring.

A state of the art stylet and cannula is described in Haaga, U.S. Pat. No. 5,718,237. Haaga describes a biopsy needle having coaxial, telescopically inter-engaged stylet, inner and outer cannulas, which are axially and rotatably displaceable relative to one another. The stylet has a distal portion provided with a cutting recess for severing a biopsy specimen from a site in a patient, and the inner cannula has a distal portion for cutting and capturing the specimen in the recess for removal from the site upon withdrawal of the needle from the patient. The distal portion of the inner cannula is partially cut away to provide an insert recess which supports a semi-circular insert of hemostatic collagen which remains at the site upon removal of the needle to minimize hemorrhagic complications by promoting blood clotting. The insert and the distal portion of the inner cannula have radially outer surfaces of corresponding radius whereby the distal portion of the inner cannula and the insert supported therein are received within the distal end of the outer cannula prior to use of the needle.

Bennett, U.S. Pat. No. 5,335,672 describes an improvement in the cocking mechanism wherein the first and second pistons are moved to their cocked positions in separate distinct operations. The improved cocking mechanism comprises an annular ring near the second end of the housing. As the annular ring is rotated, it moves the second piston into its cocked position. The knob on the first end of the housing is pulled in a direction away from the first end of the housing to move the first piston into its cocked position.

Schramm et al. U.S. Pat. No. 5,507,298 describes an apparatus for the automated and facilitated handling and operation of a biopsy needle system, having a first needle component and a second needle component. The first and second needles are provided with first and second handles, respectively, which are fitted into first and second yokes of the apparatus. The apparatus is configured to maintain the first and second needles in a first position, during insertion of the biopsy needle- point into the tissue being sampled. The apparatus is further configured to forwardly move the first and second needles into subsequent positions, respectively, in rapid, automated succession so as to segment and enclose a tissue sample, which may be tested after removal of the biopsy needle system from the tissue. A tissue sample inspection feature permits facilitated repositioning and maintenance of the lo first needle relative to the second needle after retrieval of the tissue sample to enable inspection of the retrieved tissue sample without removal of either needle from the apparatus. The apparatus is further configured so as to be actuatable form position adjacent the front or the rear of the apparatus housing.

Nottke U.S. Pat. No. 4,924,878 describes a spring-powered actuating device for operating the obturator and the cannula of a biopsy needle, and a cocking device removably attachable to the actuating device. The actuating device has a manually operated trigger slide which controls separately the release of spring-powered slides for moving the obturator and the cannula so the surgeon determines the time interval between the release of the obturator and the later release of the cannula. The extent to which the trigger slide can be displaced manually is controlled by a manually adjustable safety slide which may be set in a first position to permit the trigger slide to release the slide for the obturator only and in a second position to permit the trigger slide to release the slide for the cannula. The cocking device, when attached to the actuating device by squeezing them together manually and when so moved it retracts the slides for the obturator and the cannula to stress their springs which power them.

Akerfeldt U.S. Pat. No. 4,953,558 describes an invention referring to a driving unit for advice for tissue sampling. The device comprises in addition to the driving unit a needle unit comprising a hollow outer needle and slidably disposed therein an inner needle, the driving unit being used to propel the needles. The driving unit comprises a driving device for each mechanism adapted to be pretensioned. The driving unit in addition comprises an inner guide sleeve containing two successive needle holders adapted to be shifted in relation to each other in longitudinal direction of the sleeve and adapted to be pre-tensioned in the same direction for propelling the needles with the aid of one spring each and which are provided with releasable locking means. A manual triggering device is provided for releasing the one needle holder who in turn is adapted during the final phase of its propulsion to release the other needle holder. A tensioning sleeve which rotatable surrounds the guide sleeve is provided with cam surfaces cooperating with the needle holders to pre-tension them against he spring force.

Ohto et al., U.S. Pat. No. 5,505,211 describes the set of biopsy needles of the invention is provided with a shaft member for an inner needle which has an inner needle base at the front end to fix an inner needle, a shaft member for an outer needle which has an outer needle base at the front end to fix an outer needle, a gripping member for operation which fixes the shaft member for the inner needle and axially movable support the shaft for the outer needle, a actuating member which gives protrusion force to the shaft member for the outer needle, a holding member which holds the shaft member for the outer needle at the position before protrusion against the protrusion force of the actuating member and releases from holding the shaft member for the outer needle before protrusion by outside operation, and a rotation generating member which gives rotation force to the shaft member for the outer needle when the shaft member for the outer needle moves axially.

Taylor, U.S. Pat. No. 4,907,599 describes the soft tissue core biopsy instrument comprising a proximal outer barrel member and a distal inner barrel member, which is slidably received within the outer barrel member. A cannula driver is slidably received within the distal inner barrel member and has a distally extending cannula fixed thereto. A stylet extends distally from a stylet hub with a stylet hub being removably attached to the proximal outer barrel member. A spring is positioned within the inner barrel member between a proximal wall thereof and a proximal wall of the cannula driver for biasing the cannula driver forwardly and a latching mechanism for latching the cannula driver in a proximally retracted position against the action of spring is also provided. A trigger for unlatching the latching mechanism may be actuated to allow the spring to quickly return to its forwardly biased position, shooting or forcing the cannula driver to a distally extended position, projecting the cannula over the stylet.

Taylor, U.S. Pat. No. 4,881,551 describes the soft tissue core biopsy instrument comprises a proximal outer barrel member having a distal end and a proximal end; a distal inner barrel member which is slidably received within the outer barrel member, which has a distal end and a proximal end and which has a stop in the inner barrel member; a cannula extending distally from the inner barrel member, being fixed to the cannula driver, and having a distal tip, the cannula driver being slidably received in and movable within the inner barrel member and the inner barrel member and the cannula extending a predetermined distance out of a distal end of the inner barrel member when the instrument is in an at-rest condition; a stylet having a distal end, a proximal end, and being removable received in the outer barrel, in the inner barrel, and in the cannula, the distal end having a biopsy sample receiving notch therein; a stylet hub mounted to the proximal end of the stylet; the stylet hub being removably attached to the proximal end of the proximal outer barrel member to enable multiple biopsies to be obtained with one insertion of the cannula, the stylet extending distally from the hub and within the cannula and having a distal tip portion positioned within the cannula when the instrument is in an at-rest position and extending distally of the distal tip of the cannula in position to capture a biopsy sample when the instrument is in a cocked condition; biasing means within the inner barrel member between the stop and the cannula driver for biasing the cannula driver as the inner barrel member for latching the cannula driver in a proximally retracted cocked position within the outer barrel member and the biasing means; and a trigger, associated with the latching means, for unlatching the latching means, the trigger, upon being actuated for unlatching of the latching means, allowing the biasing means to quickly return the cannula driver and the cannula to the distally extending position thereof and over the stylet distal tip portion.

Leigh et al., U.S. Pat. No. 5,172,702 describes a soft tissue biopsy apparatus for obtaining a tissue specimen. An elongate housing has an opening at one end. A hollow cannula is positioned within the housing, is reciprocally movable there within, and one end of the needle extends through the opening for insertion into tissue from which a specimen is to be taken. A needle is positioned within the cannula, reciprocally movable there within, and also has an end extending through the opening for insertion into the tissue. This needle has a recess adjacent its outer end in which a tissue specimen is captured. The needle is connected to a slide by which the needle is moved independently of the cannula. A sleeve installed over the housing is manually operable to move the slide to a selected and cocked position prior to insertion of the cannula/needle into the tissue. Movements of the slide moves the second needle form a first position to a second position while the cannula remains stationary. A release mechanism operable by the user after the insertion of the assembly into the tissue initially returns the needle to its first position and then moves the cannula from a first position to a second position. Movement of the cannula to its second position causes the end of the cannula to cover the end of the needle to capture the tissues specimen within the recess.

The prior art teaches biopsy devices that have the following features: (i) an adjustment mechanism that allows the stroke length of the device to be adjusted, (ii) safety latches to prevent accidental firing, (iii) two overlapping and coaxially aligned coil springs, (iv) a firing mechanism that can be fired in automatic mode or in semi-automatic mode. However, the prior art does not teach a biopsy device that offers all of these features in a single compact housing. The prior art also does not teach a shock dampening device to minimize the recoil of the device when fired. The present invention fulfills these needs and provides further related advantages as described in the following summary.

SUMMARY OF THE INVENTION

The present invention teaches certain benefits in construction and use which give rise to the objectives described below.

The present invention provides a biopsy needle device having an axially elongated stylet and a cannula coaxially disposed thereabout, the stylet and cannula being mounted on stylet and cannula bases that are slidably mounted within a cavity of an elongate housing. The cavity also contains a spring-loaded firing mechanism for firing the stylet and cannula for taking a tissue sample from a patient. The stylet base contains a safety stylet latch means and a firing stylet latch means for retaining the stylet in the first, retracted position until released. The cannula base includes a safety cannula latch means and a firing cannula latch means for retaining the cannula base in the first retracted position until released. Once the safety and firing stylet latch means have been released, the stylet base advances to contact a finger of the stop pad, thereby releasing the safety cannula latch lever. The tissue of the patient prolapses into a side-facing notch of the advancing stylet. Once the firing cannula latch lever has been released, the cannula base advances to contact the stop pad, thereby causing the cannula to advance to cover the side-facing notch, thereby severing and containing the tissue. In the preferred embodiment, the stop pad transmits the force of the impact of both the stylet and cannula bases, through a longitudinal adjustment means, to a resilient diaphragm of the housing, thereby dampening the force of the impacts.

A primary objective of the present invention is to provide a biopsy needle device having advantages not taught by the prior art.

Another objective is to provide a single compact biopsy needle device that includes all of the following features: (i) an adjustment mechanism that allows the stroke length of the device to be adjusted, (ii) safety latches to prevent accidental firing, (iii) two overlapping and coaxially aligned coil springs, (iv) a firing mechanism that can be fired in automatic mode or in semi-automatic mode.

A further objective is to provide a biopsy needle device that includes a shock dampening device to minimize the recoil of the device when fired.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings.

DETAILED DESCRIPTION OF THE INVENTION

Figures 5, 5A, 5B, 5C, 5D, 6, 7:
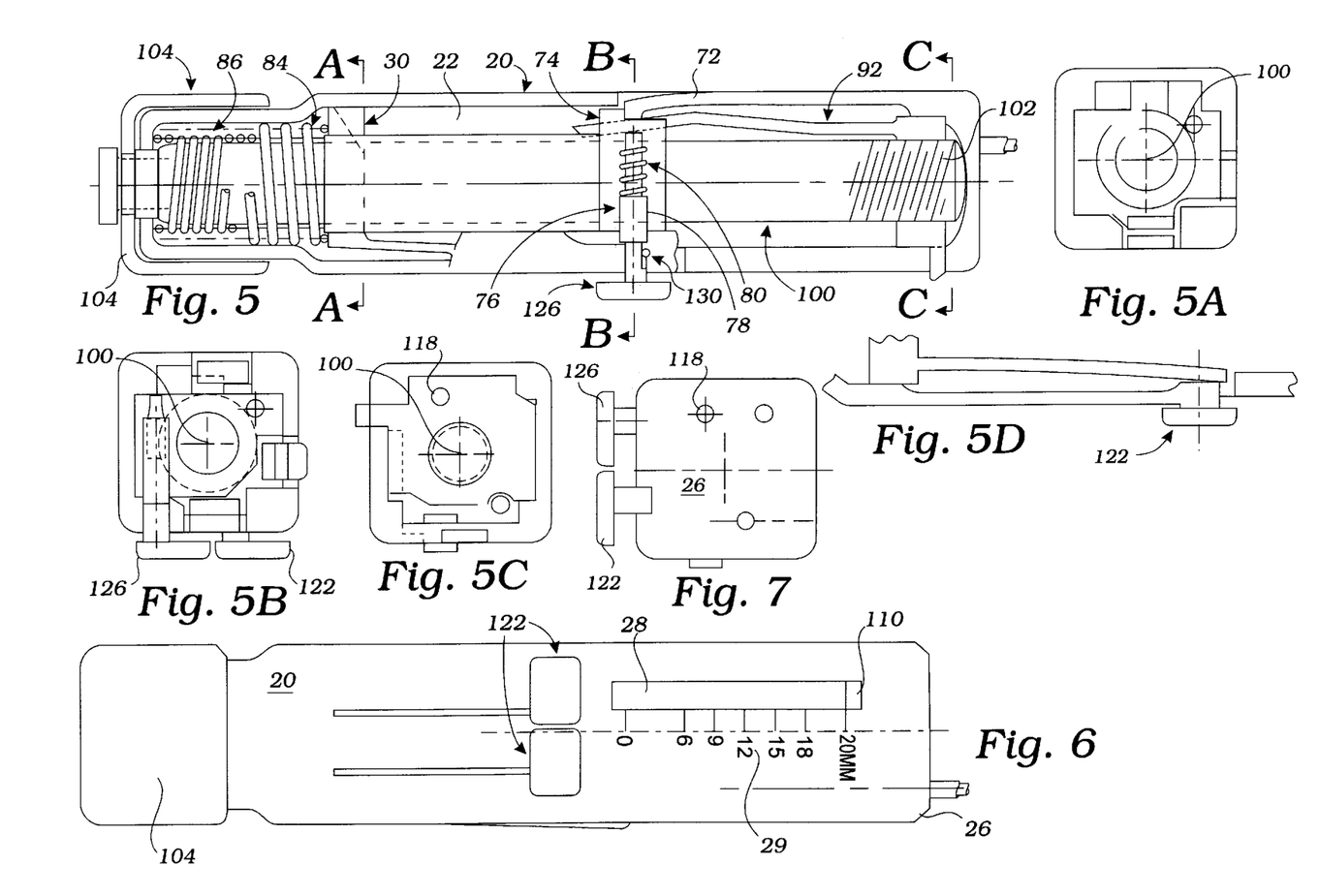
FIG. 5 is a side elevational cross section of the preferred embodiment of the invention.
FIG. 5A is a sectional view thereof taken along line A—A in FIG. 5.
FIG. 5B is a sectional view thereof taken along line B—B in FIG. 5.
FIG. 5C is a sectional view thereof taken along line C—C in FIG. 5.
FIG. 5D is a cut away view of the firing stylet latch lever.
FIG. 6 is a top plan view of the invention.
FIG. 7 is a front elevational view thereof.

The above described drawing figures illustrate the invention, a biopsy needle device 10 for taking tissue samples from a patient. As shown in FIG. 5, the biopsy needle device 10 includes an elongate housing 20 defining a cavity 22. The housing 20 is preferably constructed of lightweight plastic that is rigid but also fairly resilient. The cavity 22 is shaped to contain the spring-loaded firing mechanism 48 described more fully below. Extending from the housing 20 is an axially elongated stylet 30 having a distal end 32 and a proximal end 34 and defining a side-facing notch 36 adjacent the distal end 32. A cannula 40 coaxially disposed about the stylet 30, the cannula 40 having a distal end 42 and a proximal end 44. A typical stylet 30 and cannula 40, well known in the art, is described in Haaga, U.S. Pat. No. 5,718,237, hereby incorporated by reference in full. In use the stylet 30 is inserted into a section of tissue from which a sample is required, preferably by firing the stylet 30 into the tissue with the spring-loaded firing mechanism 48. A portion of the tissue prolapses into the side-facing notch 36 adjacent the distal end 32 of the stylet 30. The cannula 40 is then spring fired over the side-facing notch 36 to sever the tissue sample and trap it in the side-facing notch 36 for subsequent removal from the patient. It is preferred that the housing 20 and the spring-loaded firing mechanism 48 be as small and lightweight as possible so that the stylet 30 and cannula 40 can be positioned inside the patient's body in proximity to the tissue to be sampled without the weight of the device 10 causing excessive movement of the stylet 30 and cannula 40 inside the patient's body. Not only does movement of the stylet 30 and cannula 40 cause unnecessary damage to the patient's tissue, it also could cause the stylet 30 and cannula 40, when fired, to miss the target tissue and cause the biopsy to give incorrect results.

Figure 1:
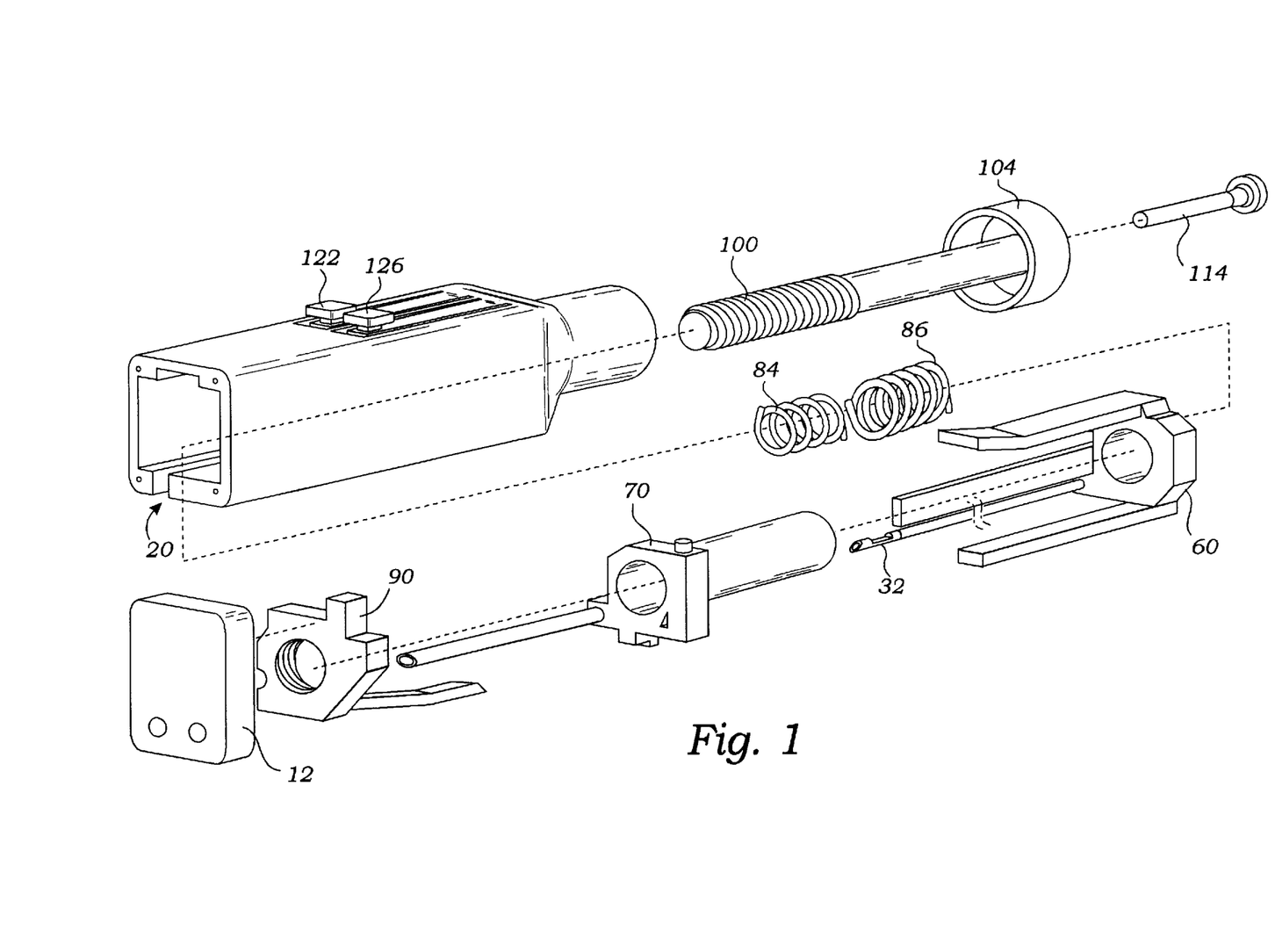
FIG. 1 is an exploded perspective view of the preferred embodiment of the present invention.
Figure 2:
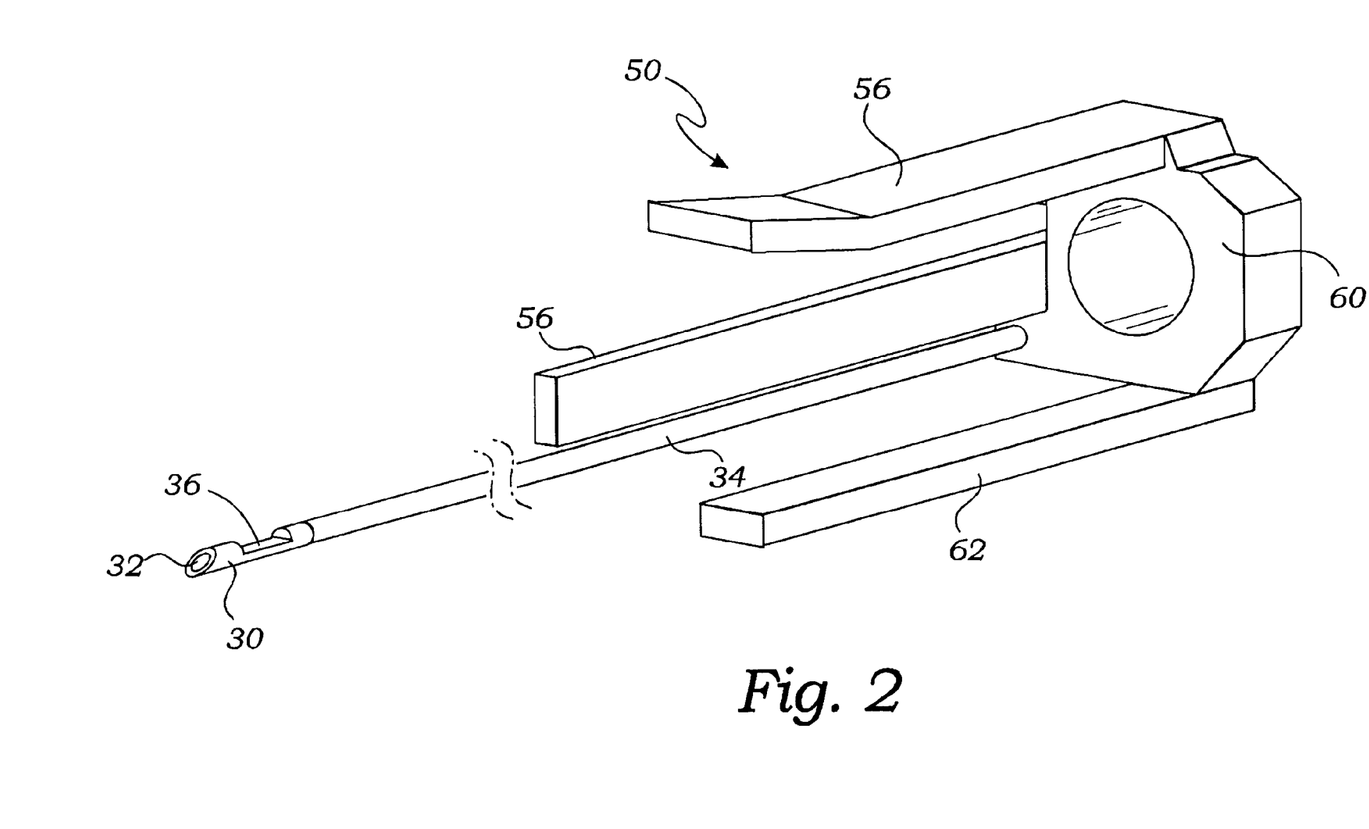
FIG. 2 is a perspective view of a stylet base.
Figures 8, 9, 10:
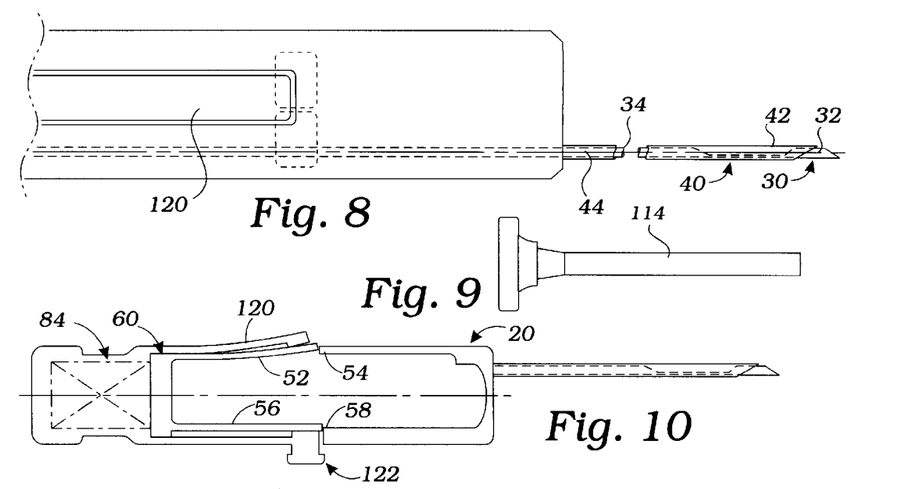
FIG. 8 is a side elevational view thereof.
FIG. 9 is a side elevational view of the retracting pin.
FIG. 10 is a side elevational cross section of the invention, showing the stylet slide with a safety stylet latch lever engaged with a safety stylet housing notch and a firing stylet latch lever engaged with a firing stylet housing notch.

As shown in FIGS. 1 and 2, a stylet base 50 is attached to the proximal end 34 of the stylet 30 and disposed in the cavity 22. Both the stylet 30 and the stylet base 50 are mounted for axial movement relative to the housing 20 and relative to the cannula 40 between a first, retracted position and a second, extended position. The stylet base 50 has a safety stylet latch means 52 for retaining the stylet 30 in the first, retracted position until released. The stylet base 50 also has a firing stylet latch means 56 for retaining the stylet 30 in the first, retracted position after the safety stylet latch means 52 has been released. The stylet base 50 also includes a wedge portion 60 described more fully below. The safety stylet latch means 52 is preferably a safety stylet latch lever. The firing stylet latch means 56 is preferably a firing stylet latch lever. The safety and firing stylet latch lever 52 and 56 are biased towards a locking position. In their locking positions, the safety stylet latch lever 52 and the firing stylet latch lever interlock with a safety stylet housing notch 54 and a firing stylet housing notch 58, respectively, to retain the stylet in the first, retracted position. As shown in FIG. 10, the safety stylet latch lever 52 preferably contacts the housing 20 at the safety stylet housing notch 54; and once the safety stylet latch lever 52 has been released, the stylet base 50 advances a small amount, thereby causing the firing stylet latch lever 56 to contact the firing stylet housing notch 58. This small movement forward prevents the safety stylet latch lever 52 from re-engaging the housing 20. Once the safety stylet latch lever 52 has been disengaged, only the firing stylet latch lever 56 restrains the stylet base 50 from moving forward.

Figure 3:
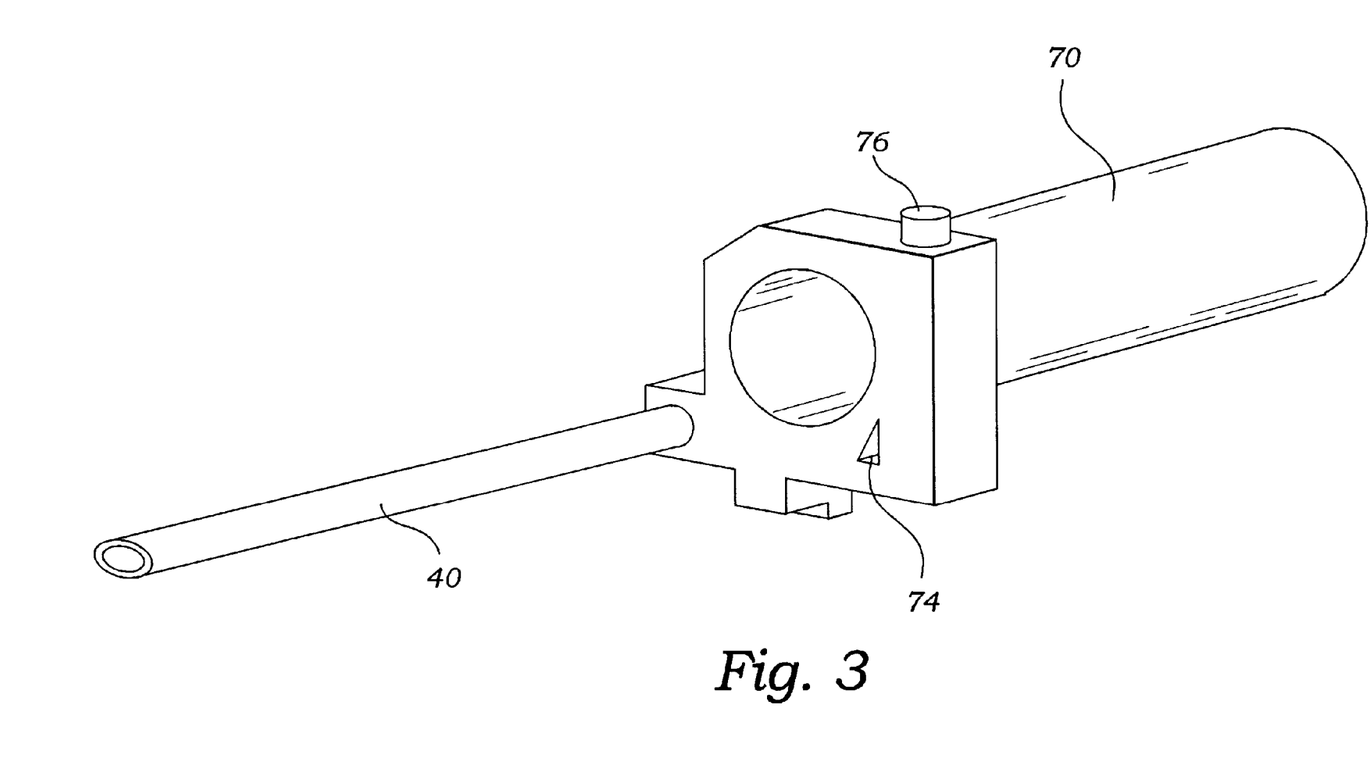
FIG. 3 is a perspective view of a cannula base.

As shown in FIGS. 1 and 3, a cannula base 70 is attached to the proximal end 44 of the cannula 40 and disposed in the cavity 22. The stylet base 50 is preferably coaxially disposed about and slidably engaging the cannula base 70, and both the cannula 40 and the cannula base 70 are mounted for axial movement relative to the housing 20, the stylet base 50, and relative to the stylet 30, between a first, retracted position and a second, extended position. The cannula base 70 has a safety cannula latch means 72 for retaining the cannula base 70 in the first retracted position until released; and the cannula base 70 has a firing cannula latch means 76 for retaining the cannula base 70 in the first retracted position until released. The safety cannula latch means 72 is preferably a safety cannula latch lever integral with the housing 20. The safety cannula latch lever 72 is preferably constructed with a resilient material, the lever 72 being biased towards a locked position in which the safety cannula latch lever 72 contacts a safety cannula notch 74 of the cannula base 70 to prevent the cannula base 70 from advancing from the first retracted position to the second extended position. Only after the stylet base 50 has moved to the second extended position, in a process described below, is the safety cannula latch lever 72 disengaged from the safety cannula notch 74. The firing cannula latch means 76 is preferably a locking cylinder that slidably engages a bore 78 in the side of the cannula base 70. The locking cylinder 76 slides between a retracted unlocking position and an extended locking position. A cylinder spring 80 biases the locking cylinder 76 towards the extended locking position. While in the extended locking position, the locking cylinder 76 contacts a cylinder notch 82 of the housing 20 to keep the cannula base 70 in the first, retracted position.

As shown in FIG. 5, the device 10 includes a means for biasing the stylet base distally 84 toward the second, extended position, and a means for biasing the cannula base distally 86 toward the second, extended position. The stylet biasing means 84 is preferably disposed about and coaxially aligned with the cannula biasing means 86. The cannula biasing means 86 is preferably a cannula coil spring, preferably a smaller left-handed coil spring. The stylet biasing means 84 is preferably a stylet coil spring, preferably a larger right-handed coil spring that is disposed about the cannula coil spring 86, which is a smaller left-handed coil spring. The opposed windings of the coil springs prevent the two coil springs 84 and 86 from becoming tangled.

Figure 4:
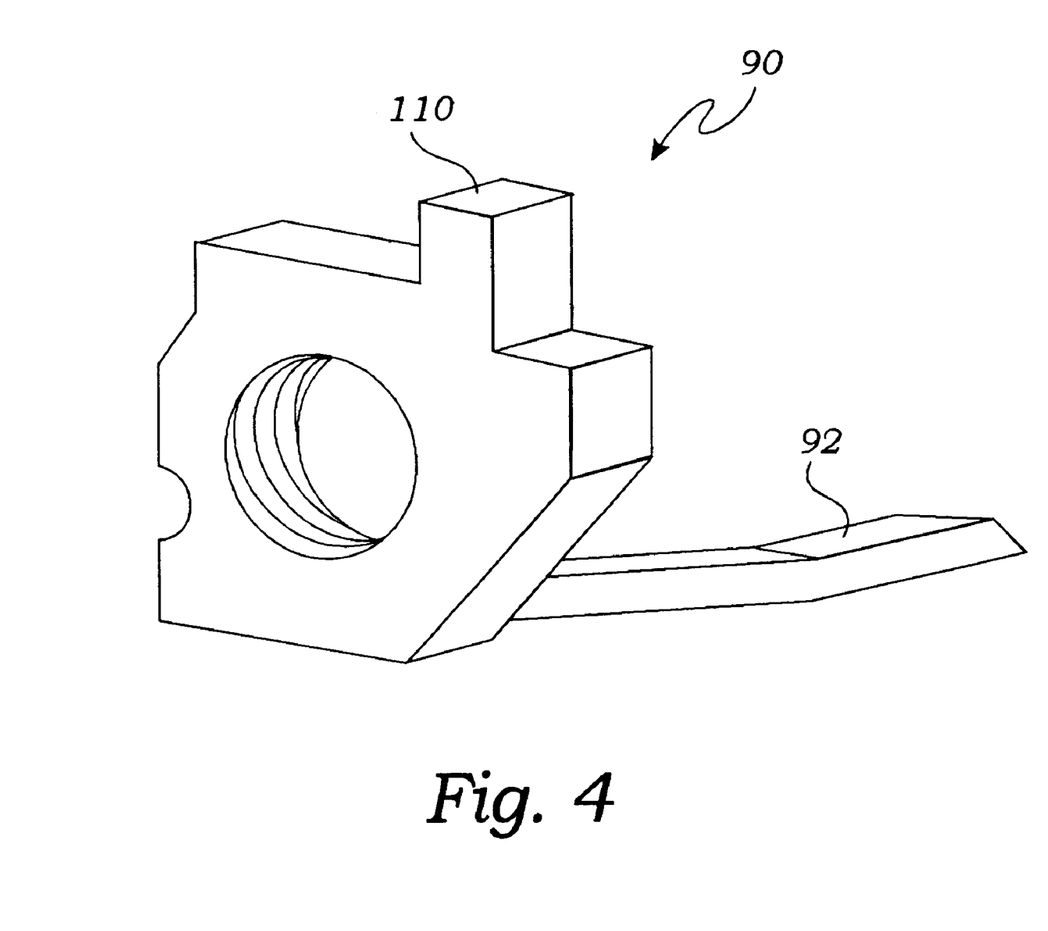
FIG. 4 is a perspective view of the stop pad.
Figure 13:
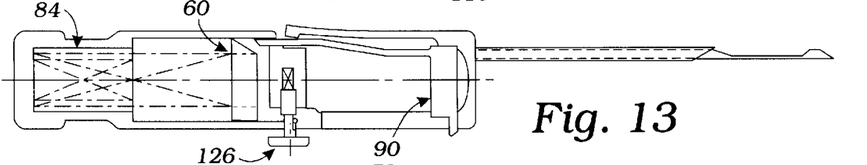
FIG. 13 is a side elevational cross section thereof after the stylet base has advanced, showing the finger contacting a wedge portion of the stylet base and acting to disengage a safety cannula latch lever from a safety cannula notch.

As shown in FIGS. 1 and 4, the device 10 includes a stop pad 90. The stop pad 90 operates to stop both the stylet base 50 and the cannula base 70 once they have moved, under the influence of the stylet and cannula coil springs 84 and 86, from the first retracted position to the second extended position. As shown in FIG. 4, the stop pad 90 has a finger 92 extending from the stop pad 90 towards the stylet base 50. The finger 92 is biased towards a locked position, but movable to an unlocked position upon contact with the wedge portion 60 of the stylet base 50. In use, when the stylet base 50 slides into the stop pad 90, the finger 92 contacts the wedge portion 60 of the stylet base 50. As shown in FIG. 13, the finger 92 is bent to the unlocked position under the influence of the wedge portion 60 and operates to retract the safety cannula latch means 72 by pushing the safety cannula latch lever 72 into the unlocked position. The stop pad 90 preferably includes a stop portion 94 that interacts with a stop finger 62 extending from the stylet base 50 to help stop the stylet base 50, so that the resilient finger 92 does not have to bear the entire brunt of the impact when the stylet base 50 crashes into the stop pad 90. Finally, the stop pad 90 has a cannula base contacting portion 96 for stopping the cannula base 70 once it reaches its extended position.

As shown in FIGS. 1 and 5, the device 10 includes a means for adjusting the longitudinal position 100 of the stop pad 90 within the cavity 22. The longitudinal adjusting means 100 is preferably an externally threaded adjusting screw positioned longitudinally within the cavity 22. A somewhat similar screw is described in Bennett, U.S. Pat. No. 5,335,672, hereby incorporated by reference in full. The stylet base 50 and the cannula base 70 are coaxially disposed about the adjusting screw 100, while the stop pad 90 is coaxially disposed about and threadedly engages the adjusting screw 100. A proximal end 102 of the adjusting screw 100 extends from a proximal end 24 of the housing 20 and terminates in a knob 104. In use, the user turns the knob 104, rotating the adjusting screw 100, and adjusting the position of the stop pad 90 within the cavity 22. The stop pad 90 preferably includes a stroke marker 110 that extends from the stop pad 90 and through a longitudinal slot 28 in the housing 20. In use, the user can adjust the length of the stroke made by the stylet 30 and cannula by turning the knob 104 and adjusting the position of the stop pad 90; and the user can view the length of the stroke with visually confirming the location of the stroke marker 110. As shown in FIG. 6, indicia 29 etched into the face of the housing 20 adjacent to the longitudinal slot 28 allow the precise adjustment of the stroke length of the stylet 30 and cannula 40. The adjusting screw 100 is preferably mounted against a resilient diaphragm 112 to dampen the impact of the stylet and cannula bases 50 and 70 against the stop pad 90. The resilient diaphragm 112 is amounted to cover an aperture in a distal end of the housing 20, with a distal end of the adjusting screw 100 abutting the resilient diaphragm 112. The shock of the stylet base 50 and the cannula base 70 hitting the stop pad 90 is transmitted through the adjusting screw 100 and absorbed by the resilient diaphragm 112.

Figure 16:
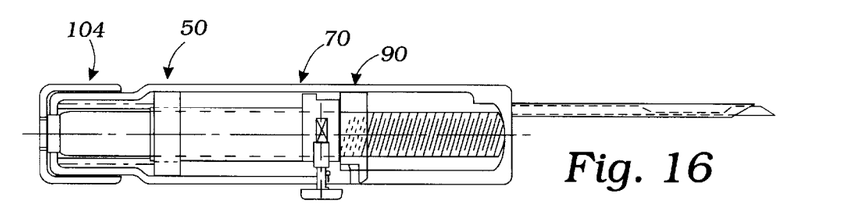
FIG. 16 is a side elevational cross section thereof, showing a knob being turned to rotate an adjusting screw, the adjusting screw retracting the stop pad to the first, retracted position.
Figure 17:
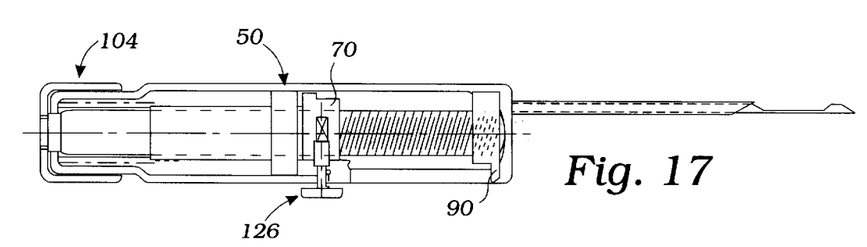
FIG. 17 is a side elevational cross section thereof, showing the adjusting screw moving the stop pad to the distal end of the housing.
Figure 18:
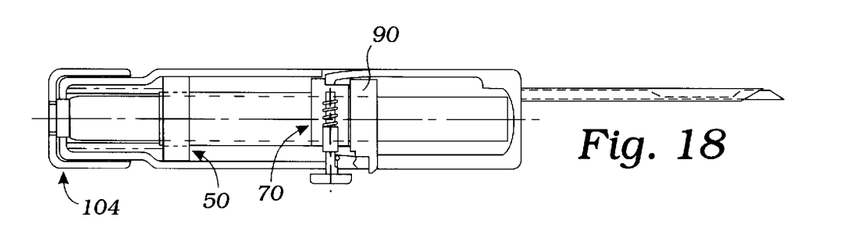
FIG. 18 is a side elevational cross section thereof, showing the stop pad being used to retract both the stylet and the cannula bases.
Figure 19:
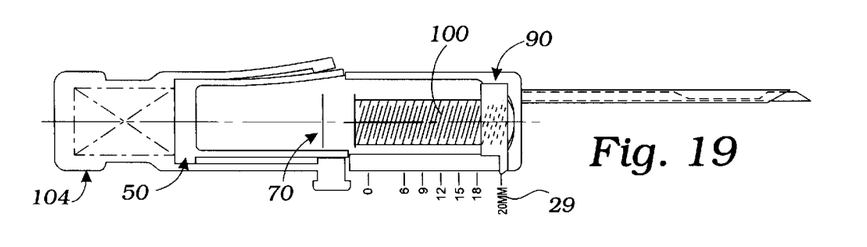
FIG. 19 is a side elevational cross section thereof, showing the knob being used to adjust the position of the stop pad, for adjusting the length of the stroke of the stylet and cannula.

The device 10 includes a means for retracting the stylet base 50 from the second extended position to the first, retracted position, for engagement of the safety stylet latch means 52 and the firing stylet latch means 56, to retain the stylet 30 in the retracted position against the stylet coil spring 84. The device 10 also includes a means for retracting the cannula base 70 from the second, extended position to the first, retracted position for engagement of the safety cannula latch means 72 and the firing cannula latch means 76, to retain the cannula base 70 in the retracted position against the cannula coil spring 86. Various devices can be devised by those skilled in the art for retracting the stylet and cannula bases 50 and 70. In one embodiment, as shown in FIGS. 7 and 9, the stylet and cannula retracting means is a retracting pin 114 that fits through a stylet retracting hole 116 and a cannula retracting hole 118, respectively, thereby allowing the user to manually push the stylet and cannula bases 50 and 70 to their first, retracted positions. When not in use, as shown in FIG. 5, the retracting pin 114 is preferably stored in a pin storage chamber 106 located in the knob 104. In the preferred embodiment, as shown in FIGS. 16 and 17, the user can also retract the stylet and cannula bases 50 and 70 by turning the adjustment knob 104 until the stop pad 90 pushes the stylet and cannula bases 50 and 70 all the way to their first, retracted positions.

Figure 11:
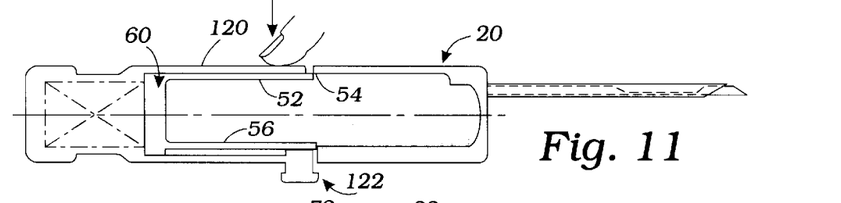
FIG. 11 is a side elevational cross sectional view thereof showing a resilient safety lever being used to disengage the safety stylet latch lever from the safety stylet housing notch.
Figure 12:
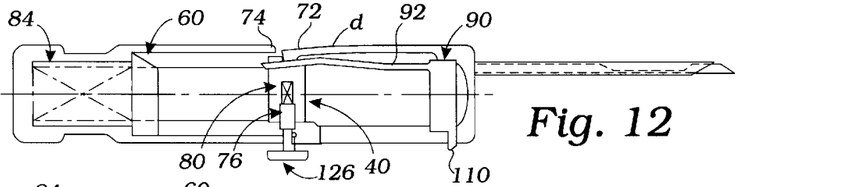
FIG. 12 is a side elevational cross section thereof, showing the stop pad with a finger extending proximally, and also showing a locking cylinder and a cannula firing button.

As shown in FIGS. 8 and 10, the device 10 includes a means for releasing 120 the safety stylet latch lever 52, preferably a resilient safety lever integral 120 with the housing 20. When pressed inwards, the resilient safety lever 120 moves the safety stylet latch lever 52 off of the safety stylet housing notch 54, allowing the stylet base 50 to advance distally. Once the stylet base 50 advances a small amount, as described above and as shown in FIG. 11, the firing stylet latch lever 52 engages the firing stylet housing notch 58, halting the further advance of the stylet base 50. As shown in FIG. 6, the device 10 further includes a means for releasing 122 the firing stylet latch lever 56, preferably a stylet firing button 122 mounted on a firing lever 124 integral with the housing 20. When pressed inwards, the stylet firing button 122 moves the firing lever 124 inwards, which moves the firing stylet latch lever 56 off of the firing stylet housing notch 58, thereby allowing the stylet coil spring 84 to advance the stylet base 50 from the first, retracted position to the second, extended position. Once the stylet base 50 has advanced, as shown in FIG. 13, the wedge portion 60 of the stylet base 50 contacts the finger 92 of the stop pad 90, causing the finger 92 to move from the locked to the unlocked position and releasing the safety cannula latch lever 72. The stop finger 62 also preferably contacts the stop portion 94 of the stop pad 90 to assist in halting the moving stylet base 50. As described above, the finger 92 flexes and acts to disengage the safety cannula latch lever 72 from the safety cannula notch 74.

Figure 14:
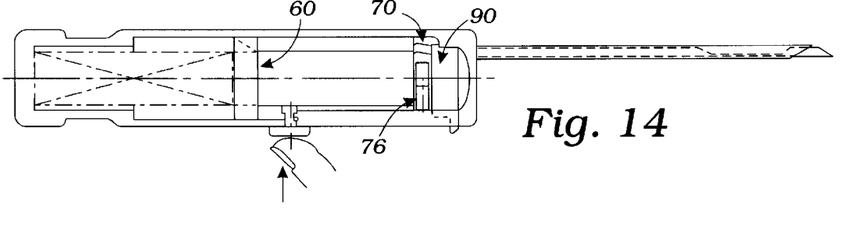
FIG. 14 is a side elevational cross section thereof, showing a cannula firing button being depressed to move a locking cylinder off of a cylinder notch and into a bore, thereby allowing the cannula base to advance.
Figure 15:
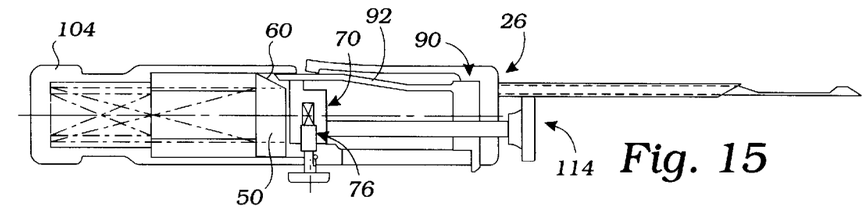
FIG. 15 is a side elevational cross section thereof, showing a retracting pin being used to push the cannula base to the first, retracted position, uncovering the tissue sample in the side-facing notch.

Once all of the above have occurred, the cannula base 70 can advance once the user activates a means for releasing the firing cannula latch means 126, to allow the cannula base 70 to move from the first, retracted position to the second, extended position. The means for releasing the firing cannula latch means 126 is preferably a cannula firing button. As shown in FIGS. 13 and 14, the cannula firing button 126 acts to depress the locking cylinder 76 into the bore 78, disengaging the locking cylinder 76 from the cylinder notch 82. The cannula firing button 126 is preferably held in place, against the bias of the cylinder spring 80, with a locking pin 130. In use, if the user presses the cannula firing button 126 at the same time he presses the stylet firing button 122, the cannula base 70 will be released as soon as the stylet base 50 reaches the second extended position and releases the safety cannula latch lever 72 (automatic firing mode). If the user wishes, however, he can wait until later to press the cannula firing button 126, and the cannula base 70 will not fire until this later time (semi-automatic firing mode). This configuration allows the user to fire both the stylet 30 and cannula 40 at precisely the desired time, without the danger of either the stylet 30 or the cannula 40 firing at the wrong time.

Once the device 10 has been fired, the stylet 30 and cannula 40 are removed from the patient's body. The cannula 40 is then retracted by inserting the retracting pin 114 through the cannula retracting hole 118 and manually retracting the cannula base 70 to the first, retracted position. Alternatively, as shown in FIGS. 16 and 17, the cannula 40 can be retracted with the adjusting screw 100. The adjusting screw 100 is used to fully retract the stylet and cannula bases 50 and 70 with the stop pad 90. The stop pad 90 is then moved distally while the safety stylet latch lever 52 and the firing stylet latch lever 56 are depressed, causing the stylet 30 to extend distally while the cannula 40 is held in the first, retracted position. Once the cannula 40 has been retracted, the tissue can be removed from the side-facing notch 36 for testing.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A biopsy needle device comprising:
   a housing defining a cavity;
   extending from the housing, an axially elongated stylet having a distal end and a proximal end and defining a side-facing notch adjacent the distal end;
   a cannula coaxially disposed about the stylet, the cannula having a distal end and a proximal end;
   a stylet base attached to the proximal end of the stylet and disposed in the cavity, the stylet and the stylet base being mounted for axial movement relative to the housing and relative to the cannula between a first, retracted position and a second, extended position, the stylet base having
      a safety stylet latch means for retaining the stylet in the first, retracted position until released,
      a firing stylet latch means for retaining the stylet in the first, retracted position after the safety stylet latch means has been released, and
      a wedge portion;
   a cannula base attached to the proximal end of the cannula and disposed in the cavity, the cannula and the cannula base being mounted for axial movement relative to the housing and relative to the stylet between a first, retracted position and a second, extended position, the cannula base having
      a safety cannula latch means for retaining the cannula base in the first retracted position until released, and
      a firing cannula latch means for retaining the cannula base in the first retracted position until released;
   a means for biasing the stylet base distally toward the second, extended position;
   a means for biasing the cannula base distally toward the second, extended position;
   a stop pad having
      a finger biased towards a locked position but movable to an unlocked position upon contact with the wedge portion of the stylet base, the finger operating to retract the safety cannula latch means when positioned in the unlocked position,
      a cannula base contacting portion for contacting the cannula base once it reaches its extended position, and
      a means for adjusting the longitudinal position of the stop pad within the cavity;
   a means for retracting the stylet base from the second extended position to the first, retracted position for engagement of the safety stylet latch means and the firing stylet latch means, to retain the stylet in the retracted position against the means for biasing the stylet distally;
   a means for retracting the cannula base from the second, extended position to the first, retracted position for engagement of the safety cannula latch means and the firing cannula latch means, to retain the cannula base in the retracted position against the means for biasing the cannula distally;
   a means for releasing the safety stylet latch means;
   a means for releasing the firing stylet latch means to allow the stylet base to move from the first, retracted position to the second, extended position, thereby causing the finger of the stop pad to contact the wedge portion, the finger moving from the locked to the unlocked position and releasing the safety cannula latch means; and
   a means for releasing the firing cannula latch means to allow the cannula base to move from the first, retracted position to the second, extended position.

2. The device of claim 1 wherein the stylet base is coaxially disposed about and slidably engaging the cannula base.

3. The device of claim 1 wherein the stylet biasing means is disposed about and coaxially aligned with the cannula biasing means.

4. The device of claim 3 wherein the cannula biasing means is a smaller left-handed coil spring, and the stylet biasing means is a larger right-handed coil spring disposed about the smaller left-handed coil spring.

5. The device of claim 1 wherein the longitudinal adjusting means is an externally threaded adjusting screw positioned longitudinally within the cavity, the stylet base and the cannula base being coaxially disposed about and the stop pad threadedly engaging the adjusting screw.

6. The device of claim 5 wherein an aperture in a distal end of the housing is covered by a resilient diaphragm; a proximal end of the adjusting screw extends from a proximal end of the housing and terminates in a knob; and a distal end of the adjusting screw abuts the resilient diaphragm, whereby turning the knob adjusts the longitudinal position of the stop pad, and the shock of the stylet base and the cannula base hitting the stop pad is transmitted through the adjusting screw and absorbed by the resilient diaphragm.

7. A method of taking a tissue sample, the method comprising the steps of:
   a) providing a biopsy needle device comprising:
      a housing defining a cavity, the housing having a safety stylet housing notch, a firing stylet housing notch, a safety cannula notch, and a cylinder notch;
      extending from the housing, an axially elongated stylet having a distal end and a proximal end and defining a side-facing notch adjacent the distal end;
      a cannula coaxially disposed about the stylet, the cannula having a distal end and a proximal end;
      a stylet base attached to the proximal end of the stylet and disposed in the cavity, the stylet and the stylet base being mounted for axial movement relative to the housing and relative to the cannula between a first, retracted position and a second, extended position, the stylet base having
         a safety stylet latch means for retaining the stylet in the first, retracted position until released,
         a firing stylet latch means for retaining the stylet in the first, retracted position after the safety stylet latch means has been released, and
         a wedge portion;
      a cannula base attached to the proximal end of the cannula and disposed in the cavity, the cannula and the cannula base being mounted for axial movement relative to the housing and relative to the stylet between a first, retracted position and a second, extended position, the cannula base having
         a safety cannula latch means for retaining the cannula base in the first retracted position until released, and, adjacent thereto, a means for releasing the safety cannula latch means, and
         a firing cannula latch means for retaining the cannula base in the first retracted position until released, and, adjacent thereto, a means for releasing the firing cannula latch means;
      a means for biasing the stylet base distally toward the second, extended position;
      a means for biasing the cannula base distally toward the second, extended position; and
      a stop pad having
         a finger biased towards a locked position but movable to an unlocked position upon contact with the wedge portion of the stylet base, the finger operating to retract the safety cannula latch means when positioned in the unlocked position,
         a cannula base contacting portion for contacting the cannula base once it reaches its extended position, and
         a means for adjusting the longitudinal position of the stop pad within the cavity;
   b) moving the stop pad proximally, with the means for adjusting the longitudinal position of the stop pad, until the safety stylet latch means engages the safety stylet housing notch, the firing stylet latch means engages the firing stylet housing notch, the safety cannula latch means engages the safety cannula notch, and the firing cannula latch means engages the cylinder notch;
   c) moving the stop pad distally, with the means for adjusting the longitudinal position of the stop pad, until the desired stroke length is achieved;
   d) pressing the means for releasing the safety stylet latch means;
   e) inserting the stylet into a patient such that the side-facing notch is adjacent to the tissue from which a biopsy is desired;
   f) pressing the means for releasing the firing stylet latch means to allow the stylet base to move distally from the first, retracted position, causing the stylet to move distally and penetrate the patient's tissue, which prolapses into the side-facing notch, also causing the finger of the stop pad to contact the wedge portion once the stylet base reaches the second, extended position, contact with the wedge portion biasing the finger from the locked to the unlocked position, thereby triggering the means for releasing the safety cannula latch means, which disengages the safety cannula latch means from the safety cannula notch;
   g) pressing the means for releasing the firing cannula latch means to allow the cannula to move from the first, retracted position to the second, extended position, thereby severing and capturing the tissue in the side-facing notch;
   h) removing the stylet and cannula from the patient's body; and
   i) retracting the cannula, thereby releasing the severed tissue for testing.

8. The method of claim 7 further comprising the step of:
   a') providing a resilient diaphragm mounted at the distal end of the housing; and
   a") mounting a distal end of the longitudinal adjusting means against the resilient diaphragm.

* * * * *